United States Patent
Ciupik et al.

(10) Patent No.: US 8,979,899 B2
(45) Date of Patent: *Mar. 17, 2015

(54) DISTANCE-KEEPING INTER-PROCESS IMPLANT

(71) Applicant: Blackstone Medical, Inc., Lewisville, TX (US)

(72) Inventors: Lechoslaw Franciszek Ciupik, Zielona Gora (PL); Robert Gunzburg, Berchem (BE); Jerzy Pieniazek, Bytom (PL); Marek Szpalski, Brussels (BE); Daniel Zarzycki, Zakopane (PL)

(73) Assignee: Blackstone Medical, Inc., Lewisville, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/850,290

(22) Filed: Mar. 25, 2013

(65) Prior Publication Data
US 2013/0238029 A1 Sep. 12, 2013

Related U.S. Application Data

(63) Continuation of application No. 13/467,914, filed on May 9, 2012, now Pat. No. 8,403,960, which is a continuation of application No. 11/992,206, filed as application No. PCT/PL2006/000059 on Sep. 1, 2006, now Pat. No. 8,241,332.

(30) Foreign Application Priority Data

Sep. 19, 2005 (PL) .......................... 377136

(51) Int. Cl.
*A61B 17/70* (2006.01)
(52) U.S. Cl.
CPC ......... *A61B 17/7067* (2013.01); *A61B 17/7065* (2013.01)

USPC .......................................... 606/249; 606/248
(58) Field of Classification Search
USPC ................................................. 606/246–279
See application file for complete search history.

(56) References Cited

U.S. PATENT DOCUMENTS

| 4,759,769 A | 7/1988 | Hedman et al. |
| 5,496,318 A | 3/1996 | Howland et al. |

(Continued)

FOREIGN PATENT DOCUMENTS

| EP | 1027004 B1 | 12/2007 |
| EP | 1030615 B1 | 12/2007 |

(Continued)

OTHER PUBLICATIONS

Williams, D.F., et al., "Implant Production and Design," Implants in Surgery, pp. 359-363 and 465-467, 1973.

(Continued)

*Primary Examiner* — Jerry Cumberledge
*Assistant Examiner* — Nicholas Plionis
(74) *Attorney, Agent, or Firm* — Baker & McKenzie LLP

(57) ABSTRACT

The invention concerns a distance-keeping inter-process implant with a body ending in its posterior part with two opposite-situated resistance protrusions. In the anterior part of the body there are situated at least two wings, at least one of which is a mobile wing connected with the body by an articulated joint. Each wing is provided with at least one guide of the tensioning band. The articulated joint between the mobile wing and the body is formed by the mutually collaborating shaped surface of the. wing (and the shaped surface of the body and is usefully secured by the pin that constitutes the axis of rotation of the mobile wing. In an alternative version of the implementation of the implant, the mobile wing connected with the body is provided with at least one arm situated with respect to the wing at the angle α amounting to from 30° to 150°.

9 Claims, 3 Drawing Sheets

(56) References Cited

U.S. PATENT DOCUMENTS

| | | |
|---|---|---|
| 6,068,630 A | 5/2000 | Zucherman et al. |
| 6,132,464 A | 10/2000 | Martin |
| 6,152,926 A | 11/2000 | Zucherman et al. |
| 6,440,169 B1 | 8/2002 | Elberg et al. |
| 6,451,019 B1 | 9/2002 | Zucherman et al. |
| 6,626,944 B1 | 9/2003 | Taylor |
| 6,761,720 B1 | 7/2004 | Senegas |
| 6,946,000 B2 | 9/2005 | Senegas et al. |
| 7,087,083 B2 | 8/2006 | Pasquet et al. |
| 7,520,887 B2 | 4/2009 | Maxy et al. |
| 7,776,069 B2 | 8/2010 | Taylor |
| 8,043,336 B2 | 10/2011 | Taylor |
| 2004/0024458 A1 | 2/2004 | Senegas et al. |
| 2005/0196420 A1 | 9/2005 | Zucherman et al. |
| 2005/0245929 A1 | 11/2005 | Winslow et al. |
| 2005/0245937 A1 | 11/2005 | Winslow |
| 2006/0064166 A1 | 3/2006 | Zucherman et al. |
| 2006/0085070 A1 | 4/2006 | Kim |
| 2006/0241601 A1 | 10/2006 | Trautwein et al. |
| 2006/0241613 A1 | 10/2006 | Bruneau et al. |
| 2006/0264938 A1 | 11/2006 | Zucherman et al. |
| 2007/0055373 A1 | 3/2007 | Hudgins et al. |
| 2009/0254185 A1 | 10/2009 | Dollinger |

FOREIGN PATENT DOCUMENTS

| | | |
|---|---|---|
| EP | 1867293 A2 | 12/2007 |
| EP | 1870049 A2 | 12/2007 |
| EP | 1889582 A2 | 2/2008 |
| JP | 2006507039 A | 3/2006 |
| JP | 2006517824 A | 8/2006 |
| PL | 354534 A1 | 1/2004 |
| WO | 9418917 A1 | 9/1994 |
| WO | 9829047 A1 | 7/1998 |
| WO | 9921501 A1 | 5/1999 |
| WO | 9940866 A1 | 8/1999 |
| WO | 9942051 A1 | 8/1999 |
| WO | 02051326 A1 | 7/2002 |
| WO | 02065954 A1 | 8/2002 |
| WO | 02071960 A1 | 9/2002 |
| WO | 03099147 A1 | 12/2003 |
| WO | 2004039243 A2 | 5/2004 |
| WO | 2004071358 A1 | 8/2004 |
| WO | 2005055868 A2 | 6/2005 |
| WO | 2006034423 A2 | 3/2006 |
| WO | 2006047562 A2 | 5/2006 |
| WO | 2006064356 A1 | 6/2006 |
| WO | 2006065774 A1 | 6/2006 |
| WO | 2006102269 A2 | 9/2006 |
| WO | 2006102428 A1 | 9/2006 |
| WO | 2006102485 A2 | 9/2006 |
| WO | 2006113080 A2 | 10/2006 |

OTHER PUBLICATIONS

The Journal of Bone and Joint Surgery, American Volume, vol. 56-A, No. 7, Oct. 1974 and Francobal Brochure, "GUEPAR total knee prosthesis," 3 pages.

Muccio, E.A., "Assembly of Plastic Parts," Plastic Part Technology, pp. 271-275, 1991.

Malloy, R., "Assembly of Injection Molded Plastic Parts, Plastic Part Design for Injection Molding—an Introduction," pp. 366 and 369, 1994.

Malloy, R., "Snap Joint Assemblies—Plastic part design for injection molding: an introduction," pp. 341-342, 1994.

Hitchon, P.W., "Techniques in Spinal Fusion and Stabilization," pp. 327 and 328, 1995.

"Clinical Background/Rationale for the Device," Department of Health and Human Services: PMA Review Memorandum dated Jul. 13, 2004.

International Search Report and Written Opinion, International Application No. PCT/PL2006/000059, dated Jan. 16, 2007, 8 pages.

International Preliminary Report on Patentability, International Application No. PCT/PL2006/000059, dated Mar. 26, 2008, 6 pages.

DISTANCE-KEEPING INTER-PROCESS IMPLANT

CROSS-REFERENCE TO RELATED APPLICATION

The present application is a continuation application of and claims priority to U.S. patent application Ser. No. 13/467,914 entitled "DISTANCE-KEEPING INTER-PROCESS IMPLANT" filed May 9, 2012, which is a continuation application of and claims priority to U.S. patent application Ser. No. 11/992,206 entitled "DISTANCE-KEEPING INTER-PROCESS IMPLANT" filed Mar. 17, 2008, which is a national phase filing under section 371 of PCT/PL2006/000059, filed Sep. 1, 2006, which claims priority to Polish Application number P.377136, filed Sep. 19, 2005, the entireties of which are hereby incorporated by reference.

BRIEF SUMMARY

The object of this invention is a distance-keeping inter-process implant applied in the surgical treatment of the spinal column with the aim of maintaining a correct distance between the spinous processes of the neighboring vertebrae and stabilization of the section of the spine involved in the treatment.

BACKGROUND

For the inter-process stabilization of the vertebral column from the posterior surgical approach, implants are applied in the form of one or several collaborating elements introduced into the inter-process space and linked with the spinous processes by means of ties in the form of a string or tape, or directly with the spinous process by means of screws, rings or other mechanical attachments. Known are also solutions in the form of elastic elements with ends specially profiled to fit the processes as well as instruments in the form of two plates embracing the lateral surfaces of the spinous processes with at least one of them linking the plates by a transverse part passing across the inter-process space.

Known from the patent description WO 99/40866 is an inter-process stabilizer for the fastening between two vertebral spinous processes. This stabilizer has the form of an elastic body consisting of two interconnected elastic parts as well as two anchoring parts in the form of arms provided with sharp protrusions fixed into the bones of the spinous processes between which the stabilizer is placed. The elastic parts of the stabilizer are shaped to a form close to at least one letter "U" or in one of the versions of the invention they have the form of a hollow cylinder with slits arranged along its axis.

An inconvenience of the described solution is the need to remove the supraspinous ligament in order to ensure a spot for the installation and fastening of the implant as well as an excessive lateral mobility of the neighboring processes. As a result of the fatigue of the material cyclically stressed during the postoperative exploitation, there also appears the risk of damage to the metallic implant.

Known from the patent description WO 99/42051 is an inter-process prosthesis consisting of an inter-process part as well as of integrated clasps jutting out in pairs on both its sides. These prosthesis clasps are considerably longer than the inter-process part in which at least one canal for the fastening of a tape linking the prosthesis with the processes is made. The prosthesis may also be placed in a fibrous pouch of the same shape with a tape constituting the implant-fastening element attached to it.

The described solution requires the separation of the soft tissues on both sides of the vertebral column as well as a rupture of the supraspinous ligament or its separation from the processes and its shifting aside during the installation of the implant, which constitutes considerable surgical invasiveness. Another inconvenience is also the absence of the possibility to regulate the distance between the clasps corresponding to the width of the spinous processes of the adjacent vertebrae as well as installation difficulties related to the setting of the prosthesis.

Known from the patent description PL354534 is the inter-vertebral implant consisting of a wedge provided with two incisures on opposite sides, intended for holding the spinous processes of two vertebrae. Each incisure is bordered by two protrusions between which the spinous process is located, and in each protrusion at least one hole is made for attaching the tie holding the wedge on the said spinous processes. The tie created from at least one tape grips a part of the surface of the spinous process, opposite to the bottom of the incisure and is tightened and subsequently blocked in a position joining the wedge permanently with the spinous processes.

An inconvenience of the application of the implant in accordance with this invention consists in the difficulties of the installation of the implant between the neighboring spinous processes, ensuring a correct arrangement stabilizing the bone-implant-tape system. A considerable invasiveness is caused by the necessity of a bilateral preparation of the soft tissues and shifting or cutting the supraspinous ligament and its fixation or reattachment after the installation of the implant.

Known from the patent description WO 03/099147 is a stabilizer constructed of two plates enveloping adjacent processes as well as a transverse link inserted between the processes and linking both plates at a definite distance from one another. The interior surfaces of the plates are provided with rings cutting into the lateral parts of the spinous processes when they approach one another along the link. One of the plates is set up on the link by means of an articulated joint and its installation with respect to the spinous processes is assured by a pin, while the other plate is fixed on the link by a processing screw.

A defect of this solution is the lack of a support for the spinous processes adapted to the inter-process space, not very stable fixation of the rings of the plates to the processes as well as a limitation of the movements of the patient and an unsatisfactory blockade of the stabilizer with respect to the spinal column.

Known from the patent description WO 2004/039243 is an implant adapted for the placement in between the spinous processes, consisting of a distance-keeping element and a means for adapting its height to the inter-process space. This implant consists of a body with a permanent wing as well as a roller upon which a distance-keeping element is set up in a rotary fashion as well as a wedge guide fastened with a screw. The distance-keeping element consists of two arms forming jointly a shape that is close to an oval and contain in between them a ball set up on a screw. This ball, when being screwed in, causes an extension of the arms of the distance-keeping element. An additional element may be another displaceable wing, also fixed on a roller beside the wedge guide.

A disadvantage of this solution is a complex design with a large number of constituent elements requiring an extensive invasive surgical access from both sides of the axis of the vertebral column. True, the design of the implant ensures the maintenance of the proper distance between the processes, but it can cause, especially when the patient bends down, excessive mobility and degradation of the bones loaded in the contact with the implant, thus limiting the time of the patient's stay in the sitting position.

Known from the patent description US 2004/0024458 is an inter-process implant in the form of a wedge with two furrows constituting the nests for the seating of the spinous processes. Between the furrows, in the central part of the wedge, there is a through hole the axis of which is parallel to the axes of the furrows. This hole constitutes from 10% to 30% of the total volume of the wedge, thanks to which the implant is susceptible to elastic deformation. In the lateral part of the wedge there are holes through which an elastic tape fixing the implant in the inter-process space is passed. A mobile element with a sharp edge, situated in a lateral niche of the wedge, serves the purpose of immobilizing the tightened tape.

The described complicated design forces the surgeon to cut or to separate extensively the soft tissues on both sides involved in fixing the spinous processes and to modify their surfaces to fit the shape of the surface of the implant. It requires also a rupture of the supraspinous ligament and carrying out complicated manipulations with a time-consuming tying up of the tension belt.

A modification of the above-described implant is the object of the invention in accordance with the patent description WO 02/071960. In this solution, two elastic tapes and two mechanisms fastening the tape are used. Apart from the inconveniences described above, the implant is characterized by a relatively large size and requires a wide surgical access arising also from the necessity of a bilateral fixation of the tensile tape.

DETAILED DESCRIPTION

Figure 1:
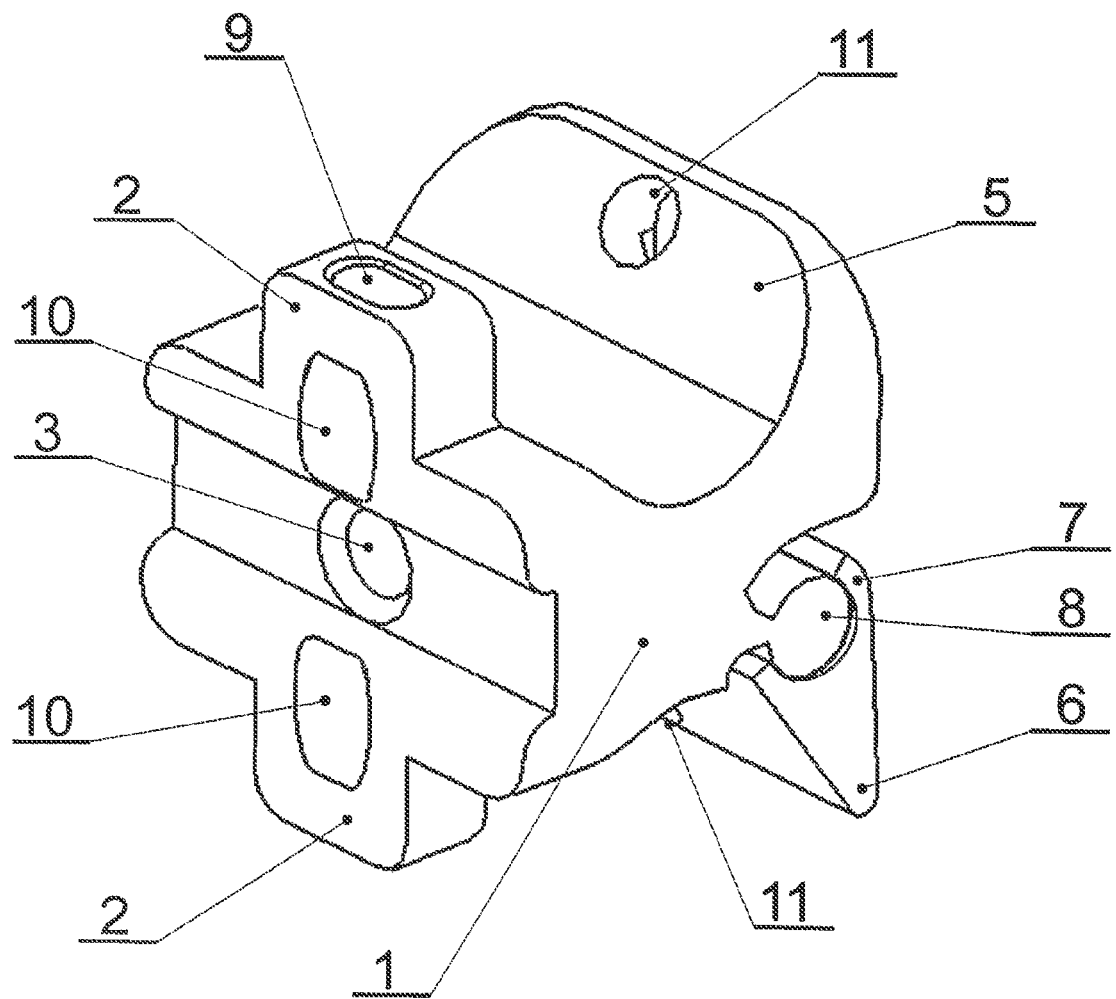
FIG. 1 illustrates an embodiment of a posterior view of a distance-keeping inter-process implant with one immobile wing in accordance with the present disclosure.

Free of the above-described inconveniences is the distance-keeping inter-process implant with a body ending in its posterior part in two opposite situated resistance protrusions provided with a means guiding the tensioning band in which, according to the invention, in the anterior part of the body there are located at least two wings, at least one of which is a wing connected with the body by a mobile articulated joint. Each wing is provided with at least one tensioning band guide.

The articulated joint of the mobile wing with the body is formed by the collaborating shaped surface of the wing and the shaped surface of the body. The useful articulated joint of the mobile wing with the body is ensured by a pin constituting the axle of the revolution of the mobile wing. The mobile wing connected with the body is provided with at least one arm situated with respect to the wing at an angle from 30° to 150°.

At least one lengthwise through hole guiding the tensioning band is made in the body. This through hole ends in the posterior part of the body with a seat for the knot formed by the ends of the tensioning band encircling the spinous processes adjacent to the implant.

The distance-keeping inter-process implant in accordance with the invention is characterized by a simple and compact design that does not require a large operational space. The easy and safe fitting in of the implant in the inter-process space shortens the operational time because for proper implant seating only a unilateral surgical access is necessary, not affecting adversely the supraspinous ligament that is essential for the maintenance of the stability of the posterior column of the spine. The bearing surfaces of the implant, their shape and dimensions, fulfill the biomechanical requirements of stabilization and fitting and are from the anatomical point of view adjusted to the shape of the spinous processes and of the space between them, thus ensuring success in the treatment of the patients from different age groups.

Figure 2:
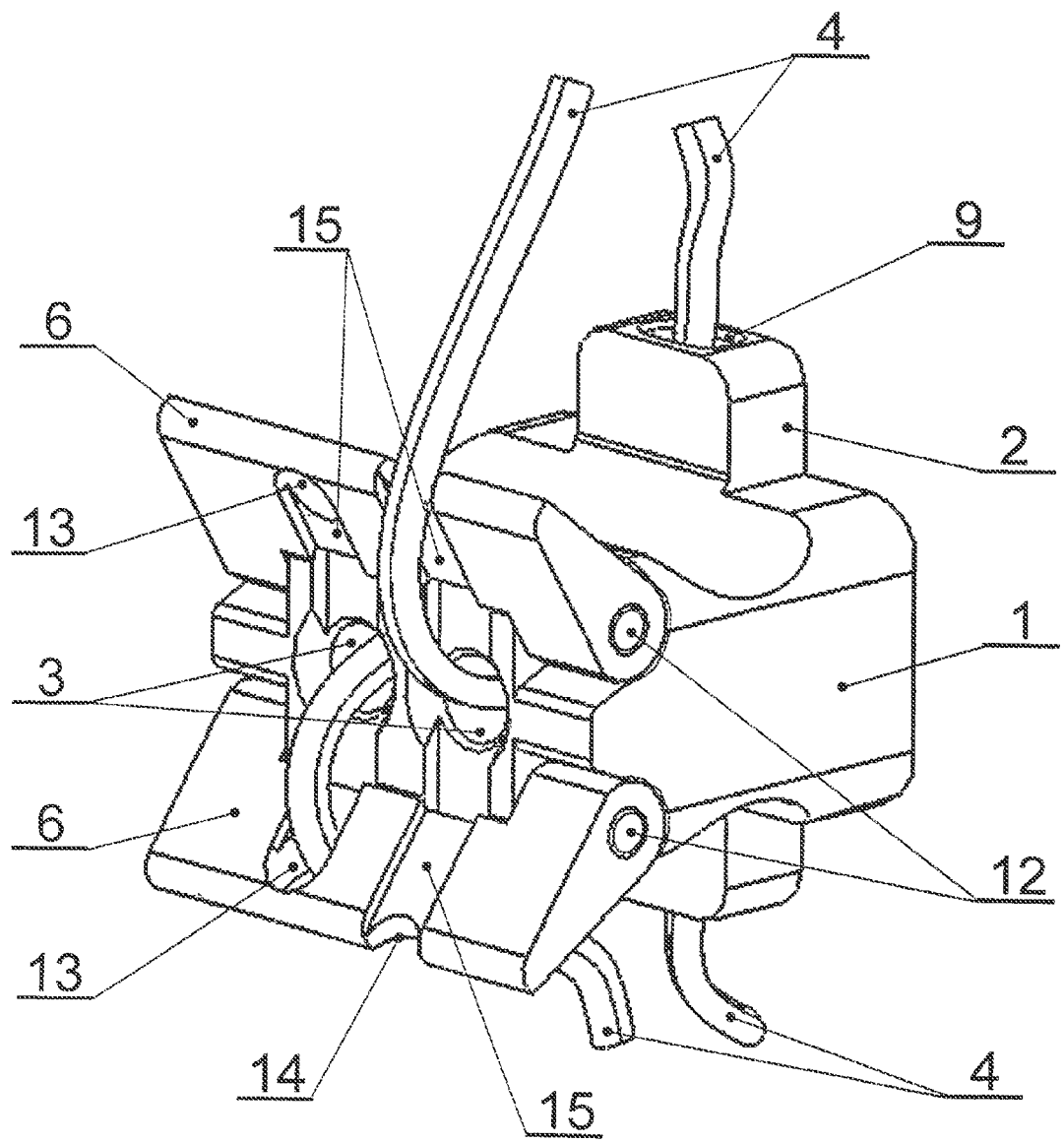
FIG. 2 illustrates an embodiment of an anterior view of a distance-keeping inter-process implant with two mobile wings in accordance with the present disclosure.
Figure 3:
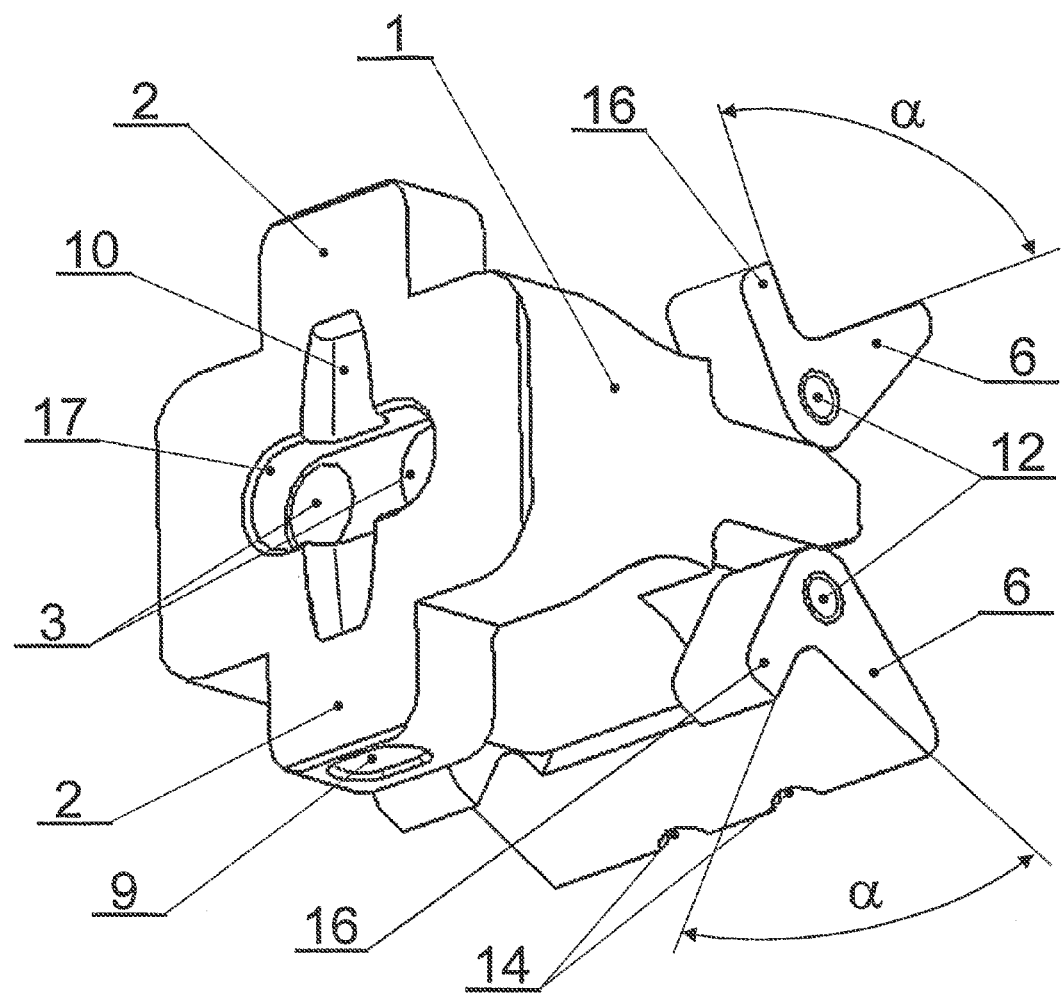
FIG. 3 illustrates an embodiment of a posterior view of a distance-keeping inter-process implant with two mobile wings with arms in accordance with the present disclosure.

The distance-keeping inter-process implant in accordance with this invention is presented in an exemplary implementation in the drawings showing in axonometric projections:

In FIG. 1 an implant with one immobile wing,

In FIG. 2 an implant provided with two mobile wings together with a collaborating tensioning band, In FIG. 3 an implant provided with two mobile wings with arms.

The distance-keeping inter-process implant presented in FIG. 1 has a body 1 ending in its posterior part with two opposite situated resistance protrusions 2. Made perpendicularly to the resistance protrusions 2 in the axis of the body 1 there is a through hole 3 for the tensioning band 4 that is not shown for the sake of simplification in FIG. 1. In the anterior part, from both sides corresponding to the resistance protrusions 2, the body 1 is provided with two wings, of which the immobile wing 5 constitutes a protrusion of the body 1 situated approximately perpendicularly to its axis, while the mobile wing 6 is provided with a shaped surface 7 constituting the bearing for the shaped surface 8 of the body 1 closely resembling a roller. The link between the two shaped surfaces 7 and 8 is formed by the articulated joint enabling a rotation of the mobile wing 6 with respect to the body 1 and an easy introduction of the implant into the inter-process space until the resistance protrusions 2 come to rest upon the spinous processes of the neighboring vertebrae of the spinal column. The resistance protrusions 2 are provided with through holes 9 and 10 constituting a means guiding the tensioning band 4. The tensioning band encircles the spinous processes adjacent to the implant and passes through the guides in the form of the holes 11 in the wings 5 and 6. After the stretching of the tensioning band 4, the mobile wing 6 is rotated to rest on the spinous process, and the ends of the tensioning band 4 are tied into a knot.

The implant shown in FIG. 2 has two mobile wings 6 connected with the body 1 by an articulated joint and secured by the pins 12 constituting the axis of rotation of the wings 6. The body 1 is provided with two through holes 3 parallel to its axis for the tensioning band 4. The resistance protrusions 2 of the body 1 are provided with the holes 9 and 10 for the tensioning band 4 similarly as in the implementation presented in FIG. 1. The mobile wings 6 guides are made for the tensioning band 4. The guides have the form of holes 13 and recesses 14 situated in the grooves 15 that also constitute the guide for the tensioning band 4.

In the implementation represented in FIG. 3, the implant has the body 1 with two mobile wings 6. In the vicinity of the articulated joint with the body 1, each wing 6 is provided on its exterior sides with two arms 16 situated with respect to the wing 6 at the angle a approaching the right angle. The body 1 is provided with two lengthwise through holes 3, and the resistance protrusions 2 are provided with the holes 9 and 10 for the tensioning band 4 not shown in FIG. 3. The holes 3 in the posterior part of the body 1 end in the seats 17 with a knot formed by the ends of the tensioning band 4. In the open state of the implant, the arms 16 of the mobile wings 6 stick out beyond the bearing surface of the body 1, and after the tensioning of the tensioning band 4 encircling the spinous processes, the arms 16 constitute an element of the bearing surface of the body 1.

What is claimed is:

1. A distance-keeping inter-process implant comprising:
  an implant body comprising a first side extending along a length of the implant body, a second side opposite the first side, a posterior region, and an anterior region opposite the posterior region, the posterior region and the anterior region separated by the length of the implant body;
  a first resistance protrusion rigidly extending in a first direction from the first side of the implant body in the posterior region of the implant body, the first resistance protrusion including a first aperture having a central axis corresponding to the first direction, and the first aperture being adapted to receive a tensioning band;
  a second resistance protrusion rigidly extending in a second direction opposite to the first direction from the second side of the implant body in the posterior region of the implant body, the second resistance protrusion including a second aperture having a central axis corresponding to the second direction, and the second aperture being adapted to receive a tensioning band;
  a first wing extending from the first side of the implant body in the anterior region of the implant body, the first wing connected to the implant body by an articulated joint, the articulated joint permitting the first wing to rotate toward a second wing, and the first wing including an end distal to the articulated joint, the end extending from the implant body in a direction away from the posterior region;
  wherein the second wing extends from the second side of the implant body in the anterior region of the implant body, the second wing connected to the implant body by an articulated joint, the articulated joint permitting the second wing to rotate toward the first wing, and the second wing including an end distal to the articulated joint, the end extending from the implant body in a direction away from the posterior region, and
  wherein each of the first and second wings comprise an aperture adapted to receive a tensioning band associated with the distance-keeping inter-process implant.

2. The distance-keeping inter-process implant of claim 1, wherein the articulated joints connecting the first and second wings to the implant body comprise a shaped surface of the implant body coupled to corresponding shaped surfaces of the first and second wings.

3. The distance-keeping inter-process implant of claim 2, wherein each of the articulated joints is attached by a pin, the pin providing an axis of rotation of the first and second wings.

4. The distance-keeping inter-process implant of claim 1, wherein the posterior end of the implant comprises a recess adapted to retain a knot formed in the tensioning band.

5. The distance-keeping inter-process implant of claim 1, wherein the aperture of the first resistance protrusion comprises a through-hole.

6. The distance-keeping inter-process implant of claim 1, wherein each of the first and second wings is rotatable to rest on a spinous process upon tensioning of the tensioning band retained in the aperture of the first or second wings.

7. The distance-keeping inter-process implant of claim 1, wherein the apertures of the first and second wings are arranged to enable the tensioning band to encircle a spinous process.

8. The distance-keeping inter-process implant of claim 1, wherein the anterior region of the distance-keeping inter-process implant is adapted for insertion into an inter-process space without adversely affecting a supraspinous ligament associated with the inter-process space.

9. The distance-keeping inter-process implant of claim 1, wherein the first and second directions are disposed on a common axis.

* * * * *